ns009974432B2

(12) United States Patent
Koshika et al.

(10) Patent No.: US 9,974,432 B2
(45) Date of Patent: May 22, 2018

(54) SCANNING ENDOSCOPE APPARATUS WITH DRIVE SIGNAL CORRECTION

(71) Applicant: OLYMPUS CORPORATION, Tokyo (JP)

(72) Inventors: Soichiro Koshika, Mitaka (JP); Kazuma Kaneko, Hachioji (JP); Masanori Sumiyoshi, Hachioji (JP); Wataru Ono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 34 days.

(21) Appl. No.: 15/374,531

(22) Filed: Dec. 9, 2016

(65) Prior Publication Data

US 2017/0086662 A1   Mar. 30, 2017

Related U.S. Application Data

(63) Continuation of application No. PCT/JP2015/060190, filed on Mar. 31, 2015.

(30) Foreign Application Priority Data

Aug. 26, 2014  (JP) .................................. 2014-171969

(51) Int. Cl.
*A61B 1/07*        (2006.01)
*A61B 1/045*       (2006.01)
(Continued)

(52) U.S. Cl.
CPC .............. *A61B 1/07* (2013.01); *A61B 1/0002* (2013.01); *A61B 1/005* (2013.01);
(Continued)

(58) Field of Classification Search
CPC ... A61B 1/07; A61B 1/00165; A61B 1/00006; A61B 1/0002; A61B 1/00057; A61B 1/00172; A61B 5/0062; G02B 26/103
See application file for complete search history.

(56) References Cited

U.S. PATENT DOCUMENTS 7,129,472 B1 * 10/2006 Okawa ............... A61B 1/00059
                                                    250/234
7,298,938 B2 * 11/2007 Johnston .............. A61B 1/0008
                                                    385/15
(Continued)

FOREIGN PATENT DOCUMENTS

EP  1 142 529 A1  10/2001
EP  3 114 982 A1   1/2017
(Continued)

OTHER PUBLICATIONS

Extended Supplementary European Search Report dated Dec. 1, 2017 in European Patent Application No. 15 83 5290.6.
(Continued)

*Primary Examiner* — John P Leubecker
(74) *Attorney, Agent, or Firm* — Scully, Scott, Murphy & Presser, P.C.

(57) ABSTRACT

A scanning endoscope apparatus includes: a light source unit; an illumination fiber inserted inside an insertion portion of an endoscope, the illumination fiber being configured to guide illuminating light from a proximal end to a distal end; an actuator configured to drive the distal end of the optical fiber so that the illuminating light outputted from the illumination fiber is scanned on a subject; a memory configured to store correlation coefficient information on a correlation coefficient between a drive signal for driving the actuator and a displacement amount of the actuator; and a controller, and the controller detects a current of the drive signal for driving the actuator and corrects the drive signal for driving
(Continued)

the actuator based on the correlation coefficient information and a value of the detected current so that the displacement amount of the actuator becomes a predetermined value.

9 Claims, 9 Drawing Sheets

(51) Int. Cl.
  *A61B 1/06* (2006.01)
  *A61B 1/00* (2006.01)
  *A61B 1/005* (2006.01)

(52) U.S. Cl.
  CPC ...... *A61B 1/00045* (2013.01); *A61B 1/00057* (2013.01); *A61B 1/00172* (2013.01); *A61B 1/045* (2013.01); *A61B 1/0661* (2013.01); *A61B 1/00006* (2013.01)

(56) References Cited

U.S. PATENT DOCUMENTS

| | | | | |
|---|---|---|---|---|
| 7,680,373 B2* | 3/2010 | Melville | ................ | G02B 7/008 |
| | | | | 2/94 |
| 8,305,432 B2* | 11/2012 | Johnston | ............ | A61B 1/00057 |
| | | | | 348/65 |
| 9,639,934 B2* | 5/2017 | Johnston | ................... | G06T 7/11 |
| 9,800,808 B2* | 10/2017 | Johnston | ................ | H04N 5/357 |
| 2006/0072843 A1* | 4/2006 | Johnston | .................. | G06K 9/20 |
| | | | | 382/254 |
| 2006/0072874 A1* | 4/2006 | Johnston | .............. | A61B 1/0008 |
| | | | | 385/25 |
| 2009/0092364 A1* | 4/2009 | Johnston | ............ | A61B 1/00096 |
| | | | | 385/117 |
| 2012/0170030 A1 | 7/2012 | Mihajlovic et al. | | |
| 2014/0210975 A1* | 7/2014 | Hirakawa | .......... | G02B 23/2423 |
| | | | | 348/68 |

FOREIGN PATENT DOCUMENTS

| | | |
|---|---|---|
| JP | 2010-534862 A | 11/2010 |
| JP | 2013-505763 A | 2/2013 |
| JP | 2014-132976 A | 7/2014 |
| JP | 2014-145942 A | 8/2014 |
| JP | 2014-150924 A | 8/2014 |
| WO | WO 2011/036598 A1 | 3/2011 |
| WO | WO 2014/119288 A1 | 8/2014 |

OTHER PUBLICATIONS

International Search Report dated Jun. 23, 2015 issued in PCT/JP2015/060190.

Japanese Office Action dated May 10, 2016 issued in JP 2015-555883.

* cited by examiner

SCANNING ENDOSCOPE APPARATUS WITH DRIVE SIGNAL CORRECTION

CROSS REFERENCE TO RELATED APPLICATION

This application is a continuation application of PCT/JP2015/060190 filed on Mar. 31, 2015 and claims benefit of Japanese Application No. 2014-171969 filed in Japan on Aug. 26, 2014, the entire contents of which are incorporated herein by this reference.

BACKGROUND OF THE INVENTION

1. Field of the Invention

The present invention relates to a scanning endoscope apparatus and specifically relates to a scanning endoscope apparatus that obtains an image by scanning a subject.

2. Description of the Related Art

Conventionally, for endoscope apparatuses in a medical field, in order to decrease a burden on examinees, various techniques for reducing a diameter of an insertion portion to be inserted into a body cavity of the examinees have been proposed. One of such proposals is, for example, a scanning endoscope apparatus including no solid-state image pickup device in a part corresponding to the aforementioned insertion portion.

For example, Japanese Patent Application Laid-Open Publication No. 2010-534862 proposes a scanning endoscope apparatus that actuates a cantilevered optical fiber using a piezoelectric actuator to move the optical fiber in a two-dimensional spiral scan pattern.

In the scanning endoscope apparatus disclosed in Japanese Patent Application Laid-Open Publication No. 2010-534862, a distal end portion of an illumination fiber configured to output illuminating light is driven so as to scan a subject in a two-dimensional spiral scan pattern, and return light from the subject is received by a light reception fiber disposed around the illumination fiber.

Then, an image of the subject is formed using signals obtained by demultiplexing the return light received by the light reception fiber into respective color components. In order to provide a small-diameter insertion portion, an actuator component such as a piezoelectric element for driving a distal end portion of a small-diameter optical fiber needs to be small.

SUMMARY OF THE INVENTION

A scanning endoscope apparatus according to an aspect of the present invention includes: a light source configured to output illuminating light; an optical fiber inserted inside an insertion portion of an endoscope, the optical fiber being configured to guide the illuminating light from the light source disposed in a main body apparatus, from a proximal end to a distal end; a dielectric actuator disposed in the endoscope, the dielectric actuator being configured to drive the distal end of the optical fiber so that the illuminating light outputted from the optical fiber is scanned on a subject; a storage section disposed in the endoscope, the storage section being configured to store correlation information on a correlation relationship between a first parameter relating to a drive signal for driving the dielectric actuator and a second parameter unique to the dielectric actuator, the second parameter relating to a displacement amount of the dielectric actuator; a drive signal detection section disposed in the main body apparatus, the drive signal detection section being configured to detect the drive signal for driving the dielectric actuator; and a correction section disposed in the main body apparatus, the correction section being configured to correct the drive signal for driving the dielectric actuator, based on the correlation information and the drive signal detected by the drive signal detection section so that the displacement amount becomes a predetermined value irrespective of an individual difference of the dielectric actuator.

DETAILED DESCRIPTION OF THE PREFERRED EMBODIMENT(S)

An embodiment of the present invention will be described below with reference to the drawings.

Figure 1:
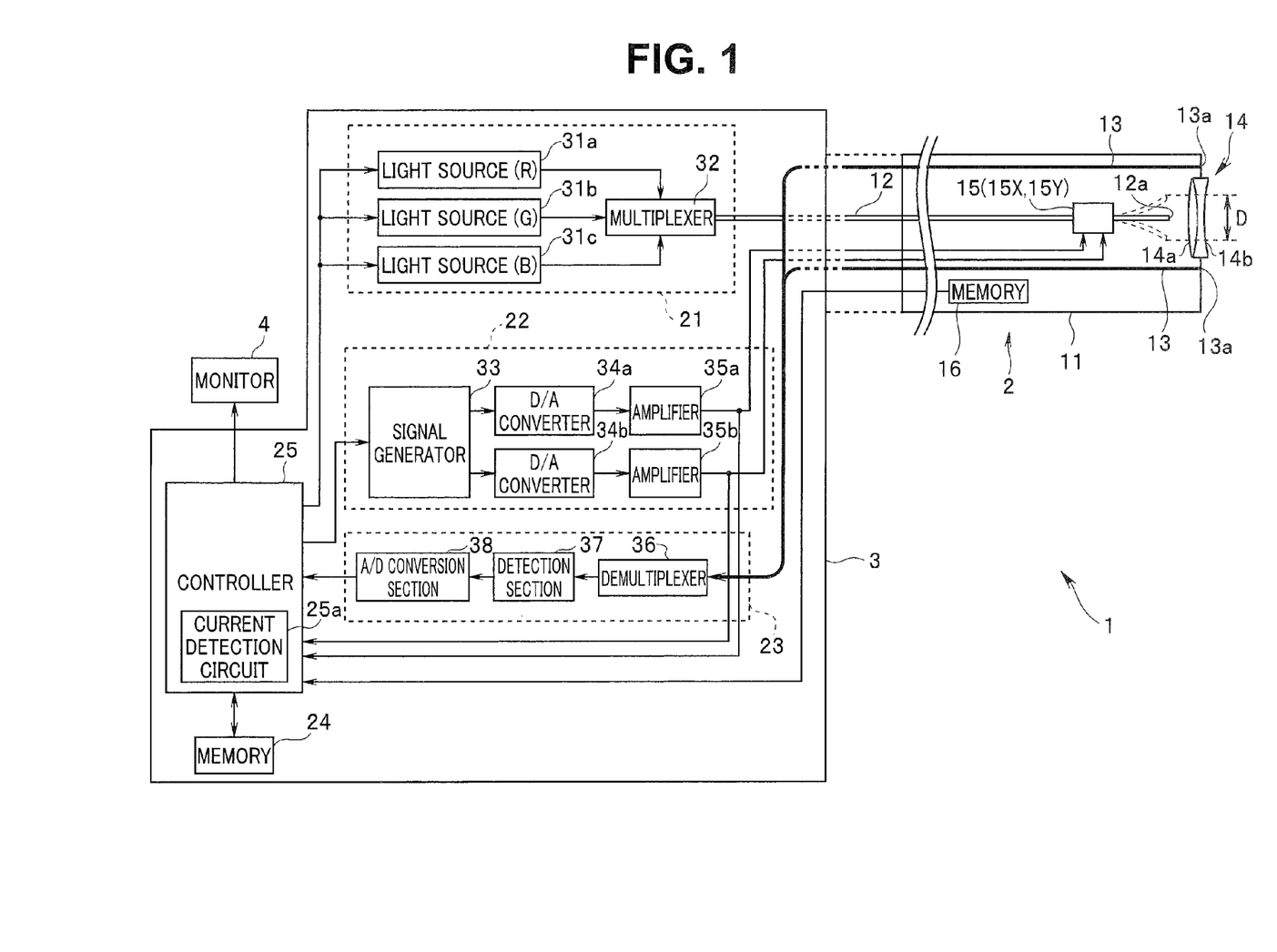
FIG. 1 is a configuration diagram illustrating a configuration of an endoscope apparatus 1 according to an embodiment of the present invention.

FIG. 1 is a configuration diagram illustrating a configuration of an endoscope apparatus 1 according to the present embodiment. As illustrated in FIG. 1, the endoscope apparatus 1 is a scanning endoscope apparatus including a scanning endoscope (hereinafter referred to as "endoscope") 2 to be inserted into a body cavity of an examinee, and a main body apparatus 3 to which the endoscope 2 is connectable.

A monitor 4 for displaying an endoscopic image is connected to the main body apparatus 3. An input apparatus (not illustrated) for operational instructions and various settings is connected to the main body apparatus 3, and a user can provide various operational instructions such as displaying, taking and/or recording of an endoscopic image to the endoscope apparatus 1 via the input apparatus.

The endoscope 2 includes an elongated and flexible insertion portion 11 that can be inserted into a body cavity of an examinee. A proximal end portion of the insertion portion 11 is detachably attachable to the main body apparatus 3.

The insertion portion 11 includes an illumination fiber 12, a light reception fiber 13, a light collection optical system 14, an actuator 15 and a memory 16. The memory 16 is a rewritable non-volatile memory such as a flash memory. The light collection optical system 14 includes lenses 14a and 14b.

The main body apparatus 3 includes a light source unit 21, a driver unit 22, a detection unit 23, a memory 24 and a controller 25.

The light source unit 21 is a light source including three light sources 31a, 31b, 31c and a multiplexer 32, and is configured to output illuminating light.

The driver unit 22 includes a signal generator 33, two digital/analog converters (hereinafter referred to as "D/A converters") 34a, 34b, and two amplifiers 35a, 35b.

The detection unit 23 includes a demultiplexer 36, a detection section 37 and an analog/digital conversion section (hereinafter referred to as "A/D conversion section") 38.

The memory 24 is a rewritable non-volatile memory such as a flash memory.

The controller 25 includes a central processing unit (CPU), a ROM and a RAM. The controller 25 provides various functions by reading and executing respective predetermined software programs stored in the ROM or the memory 24.

Various functions are provided by software programs, but may be provided by hardware circuits.

The illumination fiber 12 and the light reception fiber 13 are inserted inside the insertion portion 11 from the proximal end portion to a distal end portion. In other words, the illumination fiber 12 is an optical fiber inserted inside the insertion portion 11 of the endoscope 2, the optical fiber being configured to guide illuminating light from a proximal end to a distal end.

The illumination fiber 12 is a light guide member configured to guide illuminating light supplied from the light source unit 21 of the main body apparatus 3 to the light collection optical system 14.

The light reception fiber 13 is a light guide member configured to receive return light from a subject and guide the return light to the detection unit 23 of the main body apparatus 3. In other words, the light reception fiber 13 is an optical fiber inserted inside the insertion portion 11 of the endoscope 2, the optical fiber being configured to guide return light from a subject from a distal end to a proximal end.

An end portion of the illumination fiber 12, the end portion including a light input surface, is arranged at an output end of the multiplexer 32 provided inside the main body apparatus 3. Also, an end portion 12a of the illumination fiber 12, the end portion 12a including a light output surface, is disposed in the vicinity of a light input surface of the lens 14a provided at the distal end portion of the insertion portion 11.

An end portion 13a of the light reception fiber 13, the end portion 13a including a light input surface, is disposed and fixed around a light output surface of the lens 14b in a distal end face of the distal end portion of the insertion portion 11. Also, an end portion of the light reception fiber 13, the end portion including a light output surface, is connected to an input end of the demultiplexer 36 provided inside the main body apparatus 3.

The light collection optical system 14 includes the lens 14a configured to allow input of illuminating light passed through the light output surface of the illumination fiber 12, and the lens 14b configured to output illuminating light passed through the lens 14a to a subject.

The actuator 15 is attached to an intermediate portion of the illumination fiber 12 on the distal end portion side of the insertion portion 11. The actuator 15 is driven based on drive signals supplied from the driver unit 22 of the main body apparatus 3.

Figure 2:
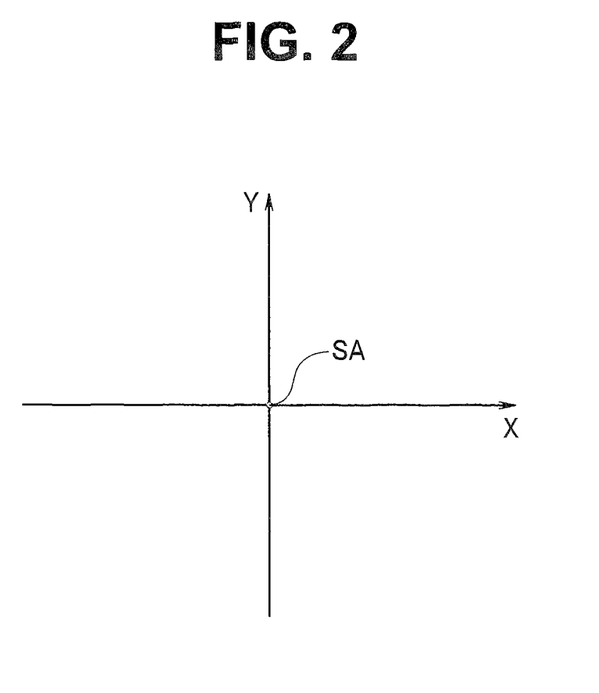
FIG. 2 is a diagram illustrating an example of an imaginary X-Y plane set on a surface of a subject, according to the embodiment of the present invention.

In the below, description will be provided taking a case where an imaginary plane perpendicular to an insertion axis (or an optical axis of the light collection optical system 14) corresponding to an axis in a longitudinal direction of the insertion portion 11 is set on a surface of a subject as an X-Y plane such as illustrated in FIG. 2, as an example.

FIG. 2 is a diagram illustrating an example of an imaginary X-Y plane set on a surface of a subject.

More specifically, point SA on the X-Y plane in FIG. 2 is indicated as a point of intersection between the insertion axis of the insertion portion 11 and the sheet where the insertion axis of the insertion portion 11 is virtually set so as to extend in a direction from the near side to the far side of the sheet. Also, an X-axis direction in the X-Y plane in FIG. 2 is set as a direction from the left side to the right side of the sheet. Also, a Y-axis direction in the X-Y plane in FIG. 2 is set as a direction from the lower side to the upper side of the sheet. Also, the X-axis and the Y-axis forming the X-Y plane in FIG. 2 intersect with each other at point SA. Point SA is a point of illumination with illuminating light when the end portion 12a of the illumination fiber 12 remains still at center position 0.

Referring back to FIG. 1, the actuator 15 includes X-axis actuator 15X configured to move so as to swing the end portion of the illumination fiber 12, the end portion including the light output surface, in the X-axis direction based on a first drive signal supplied from the driver unit 22 of the main body apparatus 3, and a Y-axis actuator 15Y configured to move so as to swing the end portion of the illumination fiber 12, the end portion including the light output surface, in the Y-axis direction based on a second drive signal supplied from the driver unit 22 of the main body apparatus 3.

Each of the X-axis actuator 15X and the Y-axis actuator 15Y includes, for example, one or more piezoelectric elements. Here, the actuators 15X and 15Y are actuators using ferroelectrics. Along with movement of the actuators 15X and 15Y such as described above, the end portion 12a of the illumination fiber 12, the end portion 12a including the light output surface, is swung in a spiral with point SA as a center. In other words, the actuator 15 is a dielectric actuator configured to, upon application of a drive voltage, drive the end portion 12a, which is the distal end of the illumination fiber 12, so as to scan illuminating light outputted from the illumination fiber 12 on the subject. The actuator 15 includes the two actuators 15X and 15Y for moving the distal end of the illumination fiber 12 in two directions perpendicular to each other.

The X-axis actuator 15X is formed by, for example, a piezoelectric element subjected to polarization treatment in advance so that a direction of polarization agrees with a negative direction of the X-axis (direction from the right to the left of the sheet of FIG. 2), and is configured to, if a voltage having a positive value is applied in response to a first drive signal outputted from the driver unit 22 (if a direction of an electric field generated as a result of supply of a drive signal is a forward direction relative to the direction of polarization), contract along a Z-axis direction (direction normal to the sheet), and if a voltage having a negative value is applied (if a direction of an electric field generated as a result of supply of a drive signal is a backward direction relative to the direction of polarization), expand along the Z-axis direction.

The Y-axis actuator 15Y is formed by, for example, a piezoelectric element subjected to polarization treatment in advance so that a direction of polarization agrees with a negative direction of the Y-axis (direction from the top to the bottom of the sheet of FIG. 2), and is configured to, if a voltage having a positive value is applied in response to a second drive signal outputted from the driver unit 22, contract along the Z-axis direction, and if a voltage having a negative value is applied, expand along the Z-axis direction.

Inside the insertion portion 11, the memory 16 configured to store information unique to the actuators 15X and 15Y, more specifically, later-described correlation coefficient information is provided. The memory 16 is connected to the controller 25 via a signal wire so that when the endoscope 2 is connected to the main body apparatus 3, the information stored in the memory 16 can be read by the controller 25 in the main body apparatus 3. The information read by the controller 25 is stored in the memory 24.

The light source 31a of the light source unit 21 includes, for example, a laser light source, and is configured to, when the light source 31a emits light under the control of the controller 25, output light in a red wavelength band (hereinafter also referred to as "R light") to the multiplexer 32.

The light source 31b includes, for example, a laser light source, and is configured to, when the light source 31b emits light under the control of the controller 25, output light in a green wavelength band (hereinafter also referred to as "G light") to the multiplexer 32.

The light source 31c includes, for example, a laser light source, and is configured to, when the light source 31c emits light under the control of the controller 25, output light in a blue wavelength band (hereinafter also referred to as "B light") to the multiplexer 32.

The multiplexer 32 is configured to multiplex the R light emitted from the light source 31a, the G light emitted from the light source 31b and the B light emitted from the light source 31c and supply the multiplexed light to the light input surface of the illumination fiber 12.

The signal generator 33 in the driver unit 22 is configured to generate, for example, a signal having a waveform such as indicated by Equation (1) below, under the control of the controller 25, as a first drive control signal for swinging the end portion 12a of the illumination fiber 12, the end portion 12a including the light output surface, in the X-axis direction, and output the signal to the D/A converter 34a. In Equation (1) below, X(t) is a signal level at a time t, a is an amplitude value not depending on the time t, and G(t) is a predetermined function used for modulation of a sine wave $\sin(2\pi ft)$.

$$X(t)=a \times G(t) \times \sin(2\pi ft) \quad (1)$$

Also, the signal generator 33 is configured to generate, for example a signal having a waveform such as indicated by Equation (2) below, under the control of the controller 25, as a second drive control signal for swinging the end portion 12a of the illumination fiber 12, the end portion 12a including the light output surface, in the Y-axis direction, and output the signal to the D/A converter 34b. In Equation (2) below, Y(t) is a signal level at a time t, b is an amplitude value not depending on the time t, G(t) is a predetermined function used for modulation of a sine wave $\sin(2\pi ft+\varphi)$, and $\varphi$ is a phase.

$$Y(t)=b \times G(t) \times \sin(2\pi ft+\varphi) \quad (2)$$

The D/A converter 34a is configured to convert the digital first drive control signal outputted from the signal generator 33 into a first drive signal, which is an analog voltage signal, and output the first drive signal to the amplifier 35a.

The D/A converter 34b is configured to convert the digital second drive control signal outputted from the signal generator 33 into a second drive signal, which is an analog voltage signal, and output the second drive signal to the amplifier 35b.

The amplifier 35a is configured to amplify the first drive signal outputted from the D/A converter 34a and output the resulting first drive signal to the X-axis actuator 15X.

The amplifier 35b is configured to amplify the second drive signal outputted from the D/A converter 34b and output the resulting second drive signal to the Y-axis actuator 15Y.

Figure 3:
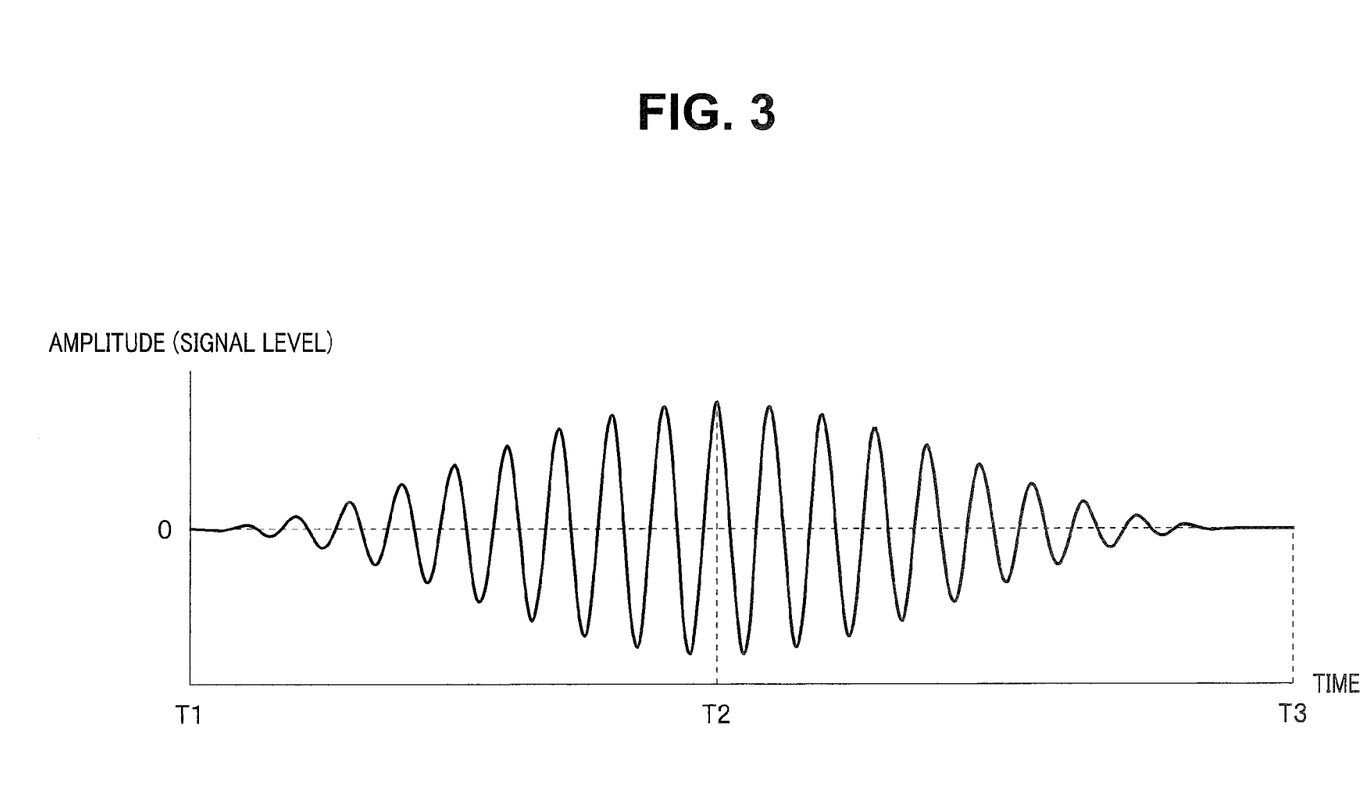
FIG. 3 is a diagram indicating an example of a signal waveform of a first drive signal supplied to an X-axis actuator 15X provided in the endoscope, according to the embodiment of the present invention.
Figure 4:
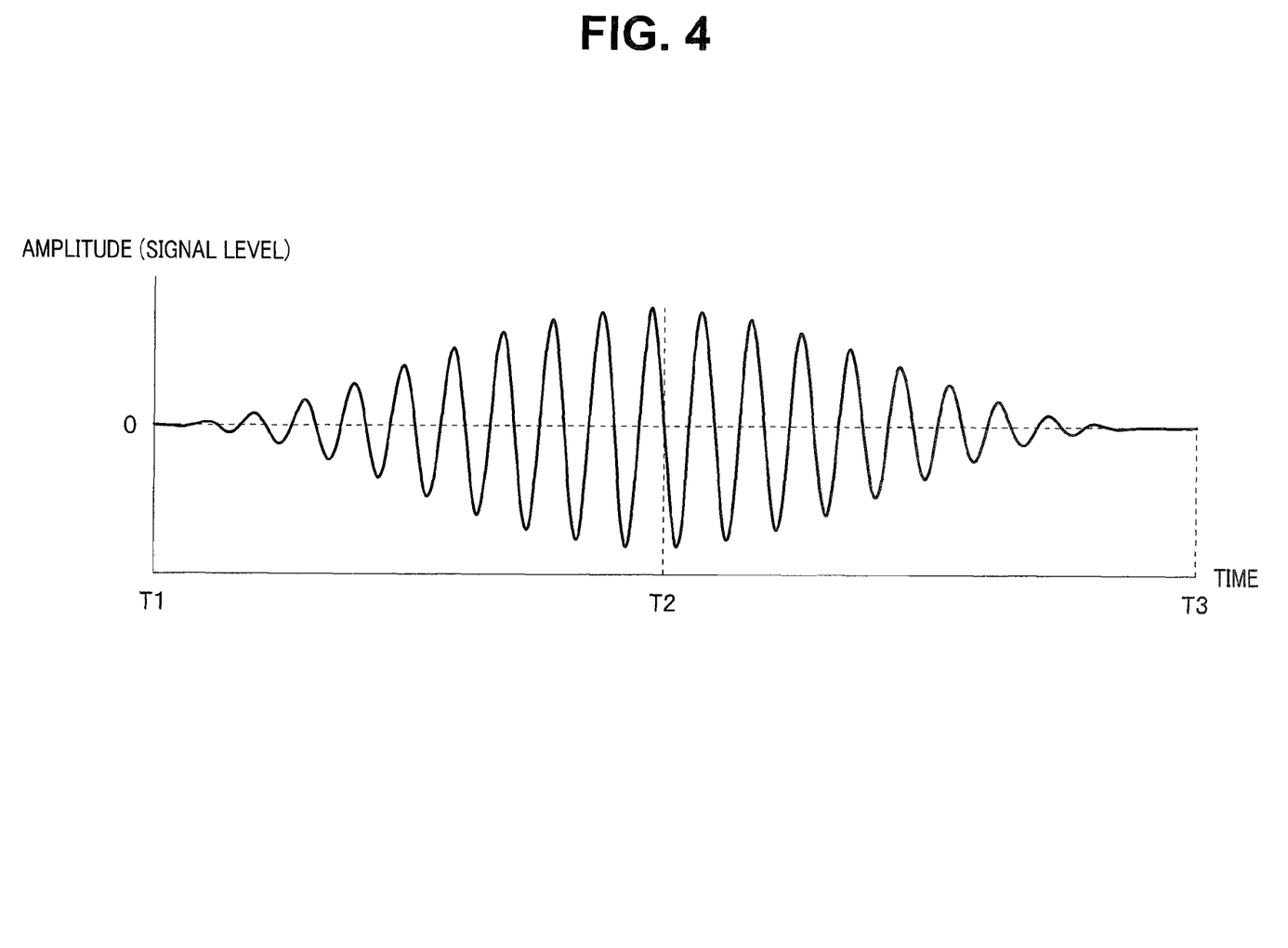
FIG. 4 is a diagram indicating an example of a signal waveform of a second drive signal supplied to a Y-axis actuator 15Y provided in the endoscope, according to the embodiment of the present invention.

Here, for example, if settings are made so that a=b and $\varphi=\pi/2$ in Equations (1) and (2) above, a first drive signal, which is a voltage signal having a signal waveform such as indicated in FIG. 3, is supplied to the X-axis actuator 15X, and a second drive signal, which is a voltage signal having a signal waveform such as indicated in FIG. 4, is supplied to the Y-axis actuator 15Y.

FIG. 3 is a diagram indicating an example of a signal waveform of a first drive signal supplied to the X-axis actuator 15X provided in the endoscope. FIG. 4 is a diagram indicating an example of a signal waveform of a second drive signal supplied to the Y-axis actuator 15Y provided in the endoscope.

Figure 5:
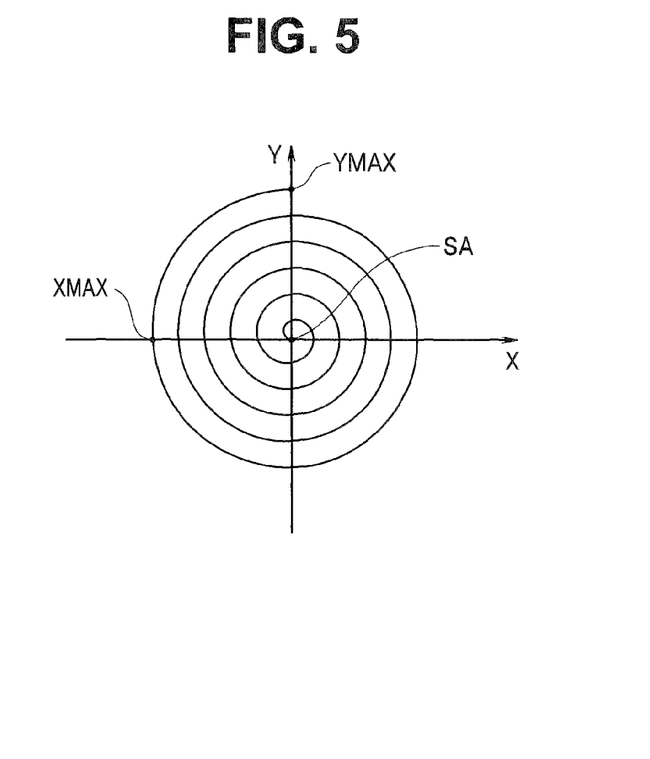
FIG. 5 is a diagram for describing temporal displacement of illumination point coordinates of illuminating light from point SA to point YMAX when the illuminating light is applied to an imaginary X-Y plane such as that in FIG. 2, according to the embodiment of the present invention.
Figure 6:
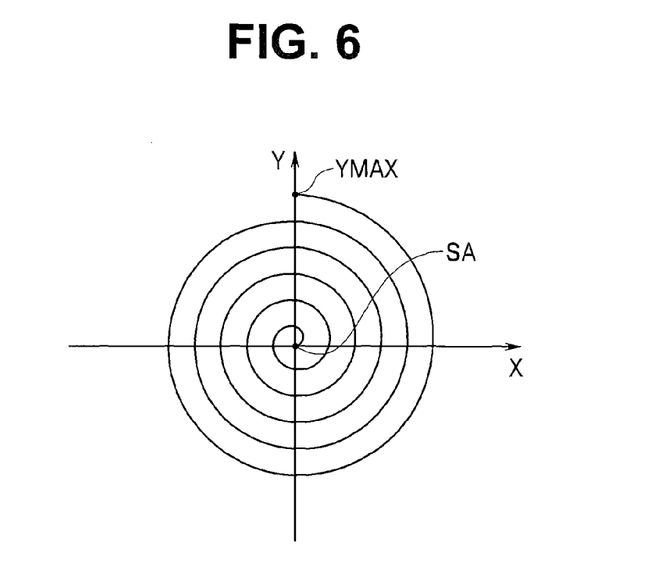
FIG. 6 is a diagram for describing temporal displacement of illumination point coordinates of illuminating light from point YMAX to point SA when the illuminating light is applied to an imaginary X-Y plane such as that in FIG. 2, according to the embodiment of the present invention.

Upon supply of a first drive signal having a signal waveform such as indicated in FIG. 3 to the X-axis actuator 15X and a second drive signal having a signal waveform such as indicated in FIG. 4 to the Y-axis actuator 15Y, the end portion of the illumination fiber 12, the end portion including the light output surface, is swung in a spiral with point SA as a center, and according to such swing, a surface of a subject is scanned in a spiral such as illustrated in FIGS. 5 and 6. In other words, the scan is a scan of illuminating light in a spiral on the subject.

FIG. 5 is a diagram for describing temporal displacement of illumination point coordinates of illuminating light from point SA to point YMAX when illuminating light is applied to an imaginary X-Y plane such as that in FIG. 2. FIG. 6 is a diagram for describing temporal displacement of illumination point coordinates of illuminating light from point YMAX to point SA when the illuminating light is applied to the imaginary X-Y plane such as that in FIG. 2.

More specifically, at a time T1 in FIGS. 3 and 4, illuminating light is applied to a position corresponding to point SA on the surface of the subject. Subsequently, with an increase of amplitude values of the first and second drive signals from the time T1 to a time T2, illumination coordinates of the illuminating light on the surface of the subject is displaced so as to draw a first spiral trajectory outward with point SA as a starting point, and furthermore, upon the time T2 being reached, the illuminating light is applied to point YMAX, which is an outermost point of the illumination coordinates of the illuminating light on the surface of the subject, from point SA. During the period from the time T1 to the time T2, the illuminating light is applied from point SA to point XMAX, which is an outermost point, in the negative X-axis direction.

Then, with a decrease of the amplitude values of the first and second drive signals from the time T2 to a time T3, the illumination coordinates of the illuminating light on the surface of the subject is displaced so as to draw a second spiral trajectory inward with point YMAX as a starting point, and furthermore, upon the time T3 being reached, the illuminating light is applied to point SA on the surface of the subject.

In other words, the actuator 15 includes a configuration that enables the end portion of the illumination fiber 12, the end portion including the light output surface, to be swung so that an illumination position of illuminating light applied to the subject via the light collection optical system 14 draws a trajectory according to the spiral scan pattern indicated as an example in FIGS. 5 and 6, based on first and second drive signals supplied from the driver unit 22.

A light output surface of the light reception fiber 13 is arranged so as to output return light outputted from the light output surface of the light reception fiber 13 to the demultiplexer 36.

The demultiplexer 36 in the detection unit 23 includes, e.g., a dichroic mirror, and is configured to demultiplex the return light outputted from the light output surface of the light reception fiber 13 into respective R (red), G (green) and B (blue) light components and output the light components to the detection section 37.

The detection section 37 detects respective intensities of the R light, the G light and the B light outputted from the demultiplexer 36, generates analog signals according to the respective detected light intensities and outputs the analog signals to the A/D conversion section 38.

The A/D conversion section 38 converts the respective analog signals outputted from the detection section 37 into respective digital signals and outputs the digital signals to the controller 25.

In the memory 24, e.g., programs for providing various functions of the main body apparatus 3 are stored. Also, in the memory 24, information on reference displacement amounts Drx, Dry, which is used in the later-described processing, is stored in advance.

The controller 25 reads control programs for light source control and actuator drive control, which are stored in the ROM or the memory 24, and performs control of the light source unit 21 and the driver unit 22 based on the read control programs.

As described above, upon the controller 25 detecting that the insertion portion 11 is electrically connected to the main body apparatus 3, the controller 25 reads information unique to the actuator 15 from the memory 16 and stores the information in the memory 24.

The controller 25 generates a drive control signal for controlling a drive signal for the actuator 15, based on the information unique to the actuator 15 and supplies the drive control signal to the driver unit 22.

Also, the controller 25 generates an image for one frame based on a R signal, a G signal and a B signal outputted from the detection unit 23 during a period corresponding to the period from the time T1 to the time T2. Also, the controller 25 generates an image for one frame based on the R signal, the G signal and the B signal outputted from the detection unit 23 during a period corresponding to the period from the time T2 to the time T3.

Here, an output of the amplifier 35a configured to output a first drive signal and an output of the amplifier 35b configured to output a second drive signal are inputted to the controller 25, and the controller 25 includes a current detection circuit 25a for detecting a current value from an inputted voltage signal for each of first and second drive signals in real time.

In other words, the current detection circuit 25a detects a magnitude of a current Ix of the first drive signal supplied to the X-axis actuator 15X and a magnitude of a current Iy of the second drive signal supplied to the Y-axis actuator 15Y, in real time.

(Correlation Coefficient Information M, N, K, L Unique to Actuator 15)

As described above, each of the X-axis actuator 15X and the Y-axis actuator 15Y is an actuator using a ferroelectric, and the respective actuators expand/contract according to respective applied voltages, but differ depending on the individual actuators. Furthermore, respective actuators have temperature characteristics, and when the actuators 15X and 15Y are being driven, displacement amounts of the respective actuators change depending on the temperatures of the respective actuators themselves.

Figure 7:
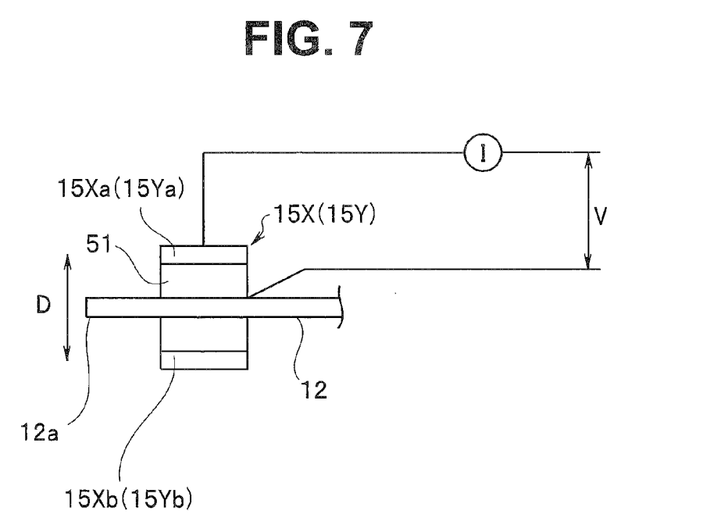
FIG. 7 is a schematic diagram illustrating a configuration of the X-axis actuator 15X according to the embodiment of the present invention.

FIG. 7 is a schematic diagram illustrating a configuration of the X-axis actuator 15X. A configuration of the Y-axis actuator 15Y is similar to that of the X-axis actuator 15X, and thus description thereof will be omitted.

Here, the actuator 15X includes two ferroelectric members 15Xa and 15Xb with a cuboidal ferrule 51 between the ferroelectric members 15Xa and 15Xb. The illumination fiber 12 is disposed in a center portion of the ferrule 51 so as to be sandwiched between the two ferroelectric members 15Xa and 15Xb.

The inner sides of the two ferroelectric members 15Xa and 15Xb are connected to a common ground, and a voltage V is applied from an outer surface of each of the ferroelectric members 15Xa and 15Xb. Currents I flowing in the respective ferroelectric members are detected by the current detection circuit 25a. In FIG. 7, only the voltage V applied to, and the current I flowing in, the ferroelectric member 15Xa are illustrated.

According to a result of a test conducted by the applicant, it turned out that in a state in which a constant voltage Vc is applied to an actuator 15 using ferroelectrics, a current I flowing in the actuator 15 changes according to the temperature T of the actuator 15 and a relationship between the current I and the temperature T is a linear relationship. It also turned out that a relationship between the temperature T and a displacement amount D of the actuator 15, which is a vibration amplitude amount of the actuator 15, is also a linear relationship.

In other words, in a state in which a constant voltage Vc is applied to the actuator 15X, the current I flowing in the actuator 15X changes according to the temperature T, and the current I flowing in the actuator 15X and the temperature T of the actuator 15X are in a linear relationship.

Figure 8:
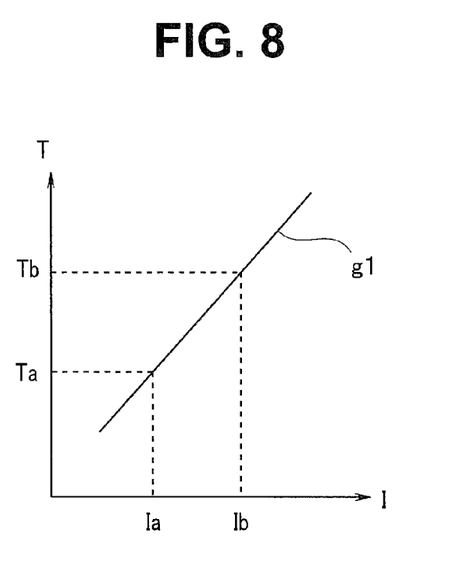
FIG. 8 is a graph g1 indicating a relationship between a temperature T and a current I of an actuator, according to the embodiment of the present invention.

FIG. 8 is a graph g1 indicating a relationship between a temperature T of an actuator and a current I. In the actuator 15X, a value of the current I flowing in the ferroelectrics when a constant voltage Vc is applied changes according to a temperature of an environment in which the actuator 15X is operating. The relationship between the current I and the temperature T indicated in FIG. 8 is a linear relationship and differs depending on the individual actuator 15X. In other words, a correlation coefficient between the current I and the temperature T differs depending on the individual actuator 15X.

Figure 9:
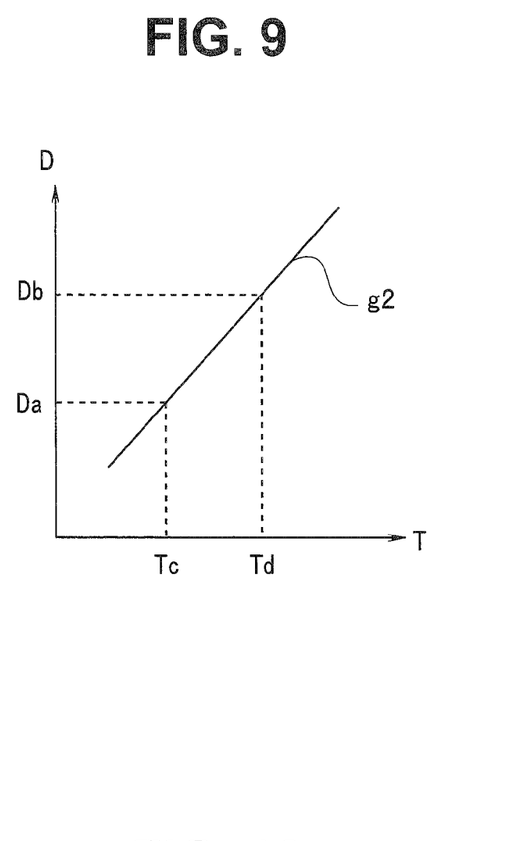
FIG. 9 is a graph g2 indicating a temperature T and a displacement amount D of an actuator, according to the embodiment of the present invention.

FIG. 9 is a graph g2 indicating a relationship between a temperature T and a displacement amount D of an actuator. As illustrated in FIG. 9, in the actuator 15X, a displacement amount D of the actuator 15X changes according to a temperature T of the actuator 15X. As illustrated in FIG. 9, when a constant voltage Vc is being applied, a relationship between the temperature T and the displacement amount D of the actuator 15X is a linear relationship and differs depending on the individual actuator 15X. The relationship between the temperature T and the displacement amount D illustrated in FIG. 9 differs depending on the individual X-axis actuator 15X. In other words, a correlation coefficient between the temperature T and the displacement amount D differs depending on the individual actuator 15X.

Therefore, at the time of manufacture of the actuator 15X, a change of a current I relative to a temperature T and a change of a displacement amount D relative to a temperature T are actually measured for each actuator, and information on a correlation coefficient between a temperature T and a current I and a correlation coefficient between a temperature T and a displacement amount D for the actuator 15X is written into the memory 16 in the endoscope 2.

The relationship between the current I and the temperature T indicated in FIG. 8 and the relationship between the temperature T and the displacement amount D indicated in FIG. 9 apply to the case of the Y-axis actuator 15Y, and at the time of manufacture of the actuator 15Y, respective changes are actually measured for each actuator, and information on respective correlation coefficients for the actuator 15Y is stored in the memory 16 in the endoscope 2.

Here, the constant voltage Vc is a voltage of a drive signal, the voltage corresponding to points XMAX and YMAX, which are outermost points of the illumination point coordinates indicated in FIG. 5 for the respective actuators 15X and 15Y.

Note that the constant voltage Vc does not necessarily need to be a voltage corresponding to points XMAX and YMAX, which are outermost points of the illumination point coordinates for the respective actuators 15X and 15Y, and may be, for example, a voltage corresponding to another point such as a point farthest next to the outermost points of the illumination point coordinates.

The main body apparatus 3 calculates a temperature T from a current I flowing in each actuator when a voltage Vc is applied, based on the correlation coefficient information in the memory 16 in the endoscope 2, and calculates a displacement amount D from the calculated temperature T.

More specifically, since the relationship between the current I and the temperature T is a linear relationship, and thus, at the time of manufacture of the actuators 15, for example, values Ia and Ib of the current I at two respective temperatures Ta and Tb are actually measured for each of the actuator 15X and the actuator 15Y when the voltage Vc is applied, a relational expression of the graph g1 in FIG. 8 is determined from the actually-measured values of the two points. The temperature T and the current I are in the relationship in Equation (3) below.

$$T = M \times I + N \quad (3)$$

Here, each of M and N is a correlation coefficient in Equation (3).

Furthermore, since the temperature T and the displacement amount D are in a linear relationship, at the time of manufacture of the actuators 15, for example, values Da and Db of the displacement amount D at two respective temperatures Tc and Td are actually measured for each of the actuator 15X and the actuator 15Y when the voltage Vc is applied, and a relational expression of the graph g2 in FIG. 9 is determined from the actually-measured values of the two points. The temperature T and the displacement amount D are in a relationship in Equation (4) below.

$$D = K \times T + L \quad (4)$$

Here, each of K and L is a correlation coefficient in Equation (4).

The four correlation coefficients M, N, K, L are values unique to each of the actuators 15X, 15Y installed in the endoscope 2, and thus are values unique to the individual endoscope 2. Values of the correlation coefficients M, N, K, L determined by actual measurement at the time of manufacture for each of the actuators 15X and 15Y when a voltage Vc is applied are stored in the memory 16 in the endoscope 2.

Therefore, the memories 16 and 24 each provide a storage section configured to store information on a correlation coefficient between a drive signal for driving an actuator 15 and a displacement amount of the actuator 15.

Figure 10:
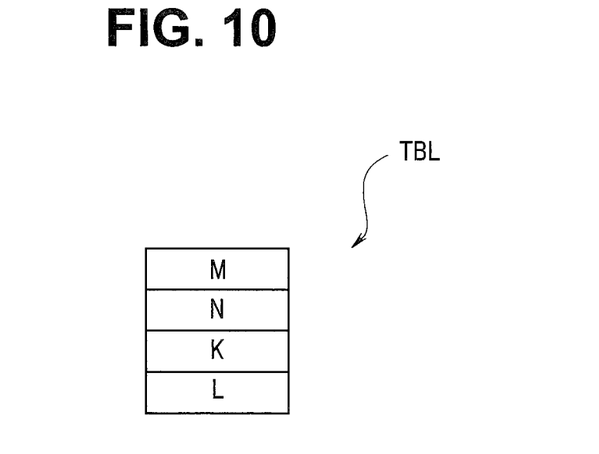
FIG. 10 is a diagram illustrating a configuration of a correlation coefficient information table TBL stored in a memory 16 in an endoscope 2, according to the embodiment of the present invention.

FIG. 10 is a diagram illustrating a configuration of a correlation coefficient information table TBL stored in the memory 16 in the endoscope 2. In the correlation coefficient information table TBL, the respective correlation coefficients M, N, K, L are stored as correlation coefficient information. In other words, the correlation coefficient information includes correlation coefficients between a drive signal (here, a current value of a current signal) and a temperature of each actuator and correlation coefficients between a temperature and a displacement amount of each actuator.

(Operation)

Next, operation of the controller 25 will be described.

When the endoscope 2 is connected to the main body apparatus 3 to observe a subject via the endoscope 2, the controller 25 controls the light source unit 21 and the driver unit 22 to generate an endoscopic image based on an image signal from the detection unit 23 and output the endoscopic image to the monitor 4, whereby an image that is, an endoscopic image of the subject is displayed.

Figure 11:
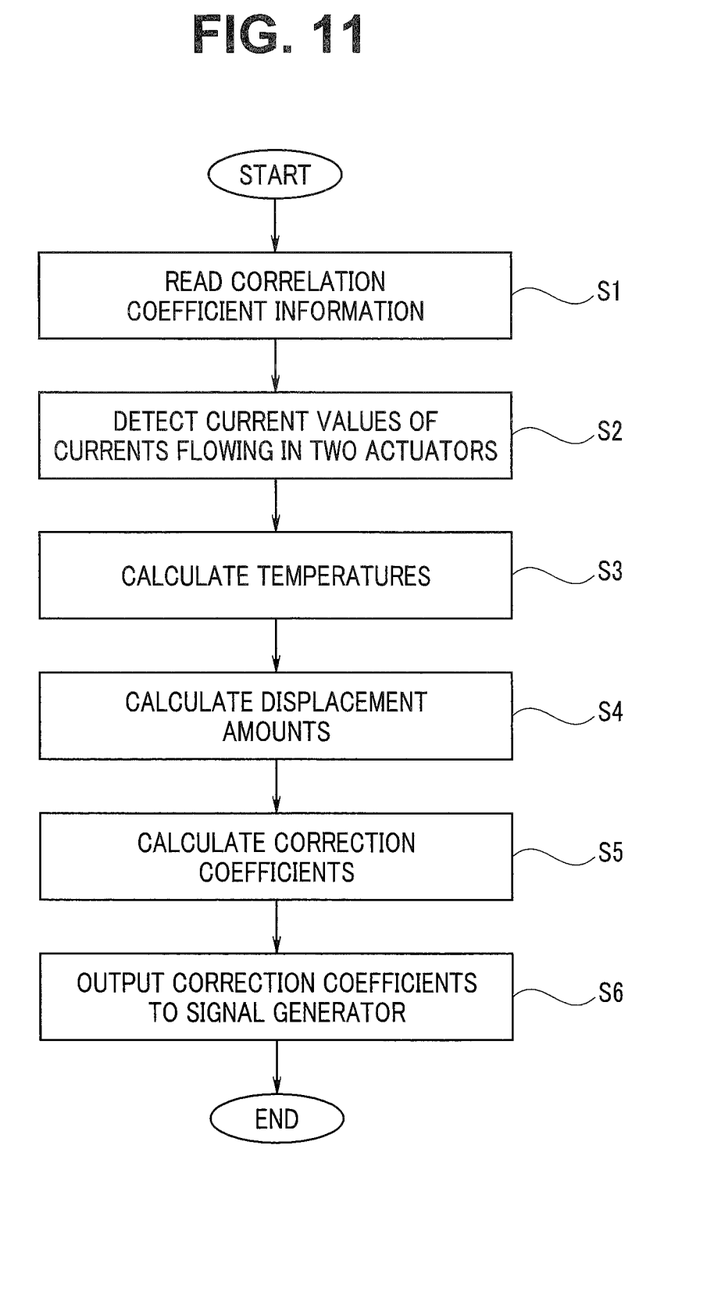
FIG. 11 is a flowchart illustrating an example of a flow of drive waveform correction processing performed by a controller 25, according to the embodiment of the present invention.

As described above, the actuator 15 has unique temperature characteristics, and a displacement amount D of the actuator 15 differs depending on the individual endoscope 2, and thus, drive waveform correction processing in FIG. 11 is performed.

FIG. 11 is a flowchart illustrating an example of a flow of drive waveform correction processing performed by the controller 25.

Upon the endoscope 2 being connected to the main body apparatus 3 and the main body apparatus 3 being powered on, the controller 25 in the main body apparatus 3 reads the correlation coefficient information on the correlation coefficient information table TBL from the memory 16 in the endoscope 2 and stores the correlation coefficient information in the memory 24 (S1).

The controller 25 detects currents Ix, Iy flowing in the respective actuators 15X, 15Y at a predetermined timing from outputs from the current detection circuit 25a (S2). Here, the predetermined timing is a timing at which the actuators 15X and 15Y are driven and a voltage Vc corresponding to points XMAX and YMAX, which are outermost points of the illumination point coordinates, is applied.

In other words, the processing in S2 provides a drive signal detection section configured to detect first and second drive signals for the actuators 15X and 15Y, which are dielectric actuators, and current values of current signals flowing in the actuators 15X and 15Y are detected.

The controller 25 calculates and estimates respective temperatures Tx and Ty of the respective actuators 15X and 15Y based on the detected values of the currents Ix, Iy flowing in the actuators 15X and 15Y, respectively (S3). The calculation of the temperatures Tx and Ty is performed using Equation (3) above and the correlation coefficients M, N stored in the memory 24.

Furthermore, the controller 25 calculates and estimates respective displacement amounts Dx and Dy of the actuators 15X and 15Y from the calculated temperatures Tx and Ty (S4). The calculation of the displacement amounts Dx and Dy is performed using Equation (4) above and the correlation coefficients K, L stored in the memory 24.

The controller 25 calculates correction coefficients Adx and Ady for the first and second drive signals from the calculated and estimated displacement amounts Dx and Dy so that the respective displacement amounts Dx and Dy of the actuators 15X and 15Y become respective predetermined displacement amounts Drx and Dry (S5).

More specifically, the controller 25 calculates the correction coefficient Adx for the actuator 15X from the displacement amount Dx obtained by the calculation and the reference displacement amount Drx, which is a reference. The reference displacement amount Drx is a displacement amount at the time of maximum displacement in the X-axis direction for obtaining a spiral illumination range of a predetermined size, and is stored in advance in the memory 24. Here, the correction coefficient Adx is calculated according Equation (5) below.

$$Adx=Dx/Drx \qquad (5)$$

The correction coefficient Adx is a ratio of the displacement amount Dx relative to the reference displacement amount Drx for the actuator 15X.

Figure 12:
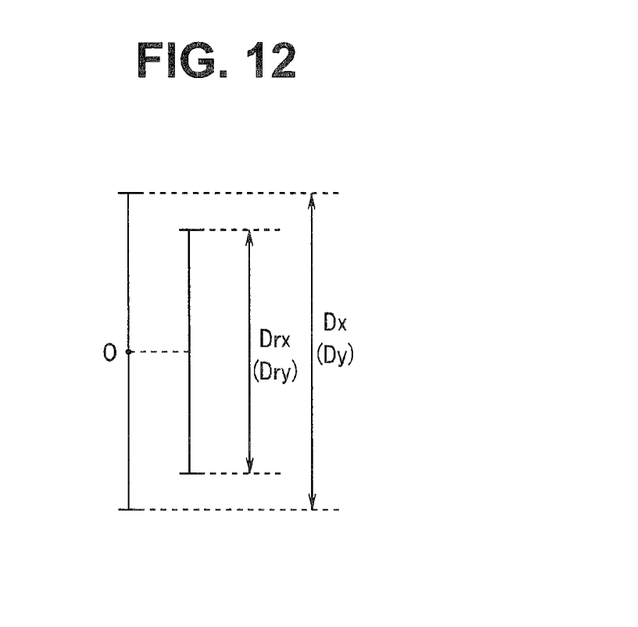
FIG. 12 is a diagram for describing a relationship between a calculated displacement amount Dx and a reference displacement amount Drx, according to the embodiment of the present invention.

FIG. 12 is a diagram for describing a relationship between the calculated displacement amount Dx and the reference displacement amount Drx. FIG. 12 indicates a displacement range of each of the calculated displacement amount Dx and the reference displacement amount Drx relative to the center position 0 when the end portion 12a of the illumination fiber 12, the end portion 12a including the light output surface, remains still. In the example in FIG. 12, the calculated displacement amount Dx is large compared to the reference displacement amount Drx.

Likewise, the correction coefficient Ady can be calculated according to Equation (6) below.

$$Ady=Dy/Dry \qquad (6)$$

The correction coefficient Ady is a ratio of the displacement amount Dy relative to the reference displacement amount Dry for the actuator 15Y. The reference displacement amount Dry is a displacement amount at the time of maximum displacement in the Y-axis direction for obtaining a spiral illumination range of a predetermined size, and is stored in advance in the memory 24. A relationship between the calculated displacement amount Dy and the reference displacement amount Dry is similar to that in FIG. 12.

When the displacement amounts Dx and Dy change according to a temperature of an environment in which the endoscope 2 is used, a swing range of the illuminating light changes. If the swing range changes according to the environment temperature during endoscopic observation, an endoscopic image displayed on the monitor 4 looks differently, which makes a surgeon feel odd.

Figure 13:
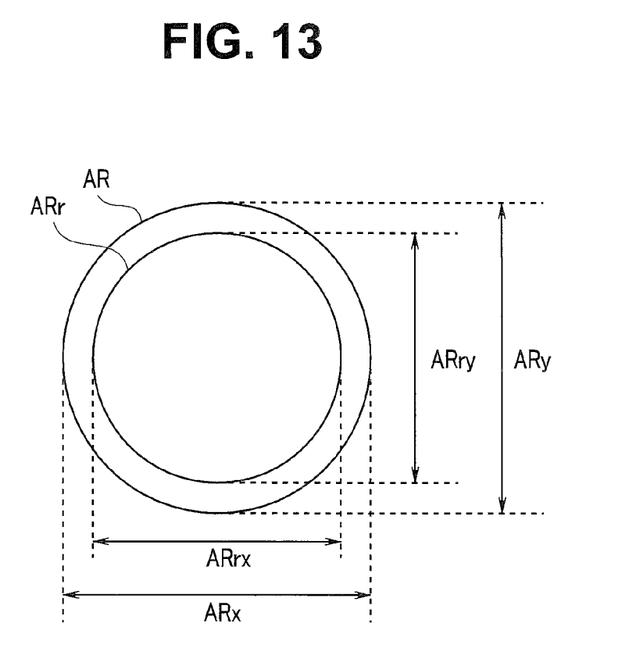
FIG. 13 is a diagram indicating a change of an illumination range of illuminating light due to a change of displacement amounts Dx and Dy, according to the embodiment of the present invention.

FIG. 13 is a diagram indicating a change of an illumination range of illuminating light due to a change of the displacement amounts Dx and Dy. In FIG. 13, a reference illumination range ARr is an area in which illuminating light is applied in a spiral when the end portion 12a of the illumination fiber 12 is displaced by the reference displacement amounts Drx and Dry of the actuators 15X and 15Y. The illumination range AR indicates an area in which illuminating light is applied in a spiral when the end portion 12a of the illumination fiber 12 is displaced by the displacement amounts Dx and Dy of the actuators 15X and 15Y.

As described above, the reference displacement amounts Drx and Dry are maximum displacement amounts at the time of maximum displacement in two respective X-axis and Y-axis directions for obtaining a spiral illumination range of a predetermined size. In FIG. 13, the illumination range AR formed by the displacement amounts Dx and Dy changed by the temperature of the actuator 15 is larger than the illumination range ARr formed by the reference displacement amounts Drx and Dry. Here, in FIG. 13, diameters ARx and ARy of the illumination range AR are larger than diameters ARrx and ARry of the reference illumination range ARr, respectively, but may be small depending on the temperature.

The controller 25 outputs the correction coefficients Adx and Ady calculated from Equations (5) and (6) above to the signal generator 33 (S6).

The signal generator 33 generates first and second drive control signals corrected based on the correction coefficients Adx and Ady from the controller 25 and outputs the first and second drive control signals to the D/A converter 34a.

For example, the signal generator 33 generates a drive control signal by multiplying a drive control signal for the X-axis actuator 15X by the above-described correction coefficient Adx, and generates a drive control signal by multiplying a drive control signal for the Y-axis actuator 15Y by the above-described correction coefficient Ady. Consequently, waveforms of the drive signals to be outputted by the signal generator 33 are corrected.

Therefore, the drive control signal for the actuator 15X is corrected by the correction coefficient Adx and the drive control signal for the actuator 15Y is corrected by the correction coefficient Ady, whereby the displacement amounts Dx and Dy become equal to the reference displacement amounts Drx and Dry, respectively. As a result, the illumination range AR becomes equal to the reference illumination range ARr, and a size of the subject formed in the detection unit 23 from light inputted to the light input surface of the light reception fiber 13 and displayed on the monitor 4 does not fluctuate.

In other words, in the processing in S6, each of output levels of the drive control signals is corrected based on the ratio of the relevant displacement amount calculated from the relevant current value detected in S2, using the correlation coefficient information, relative to the relevant reference displacement amount, whereby the first and second drive signals for driving the actuator 15 are corrected. In S6, the first and second drive signals for driving the actuators 15X and 15Y are corrected based on the correlation coefficient information and the current values detected in S2 so that the displacement amounts of the actuators 15X and 15Y at the time of maximum displacement become the reference displacement amounts Drx and Dry, respectively.

Therefore, the processing in S6 provides a correction section configured to correct the first and second drive signals for driving the actuator 15 based on the correlation coefficient information and the current values detected in S2 so that the displacement amounts Dx and Dy of the actuator 15, which is a dielectric actuator, become the respective reference displacement amounts Drx and Dry, which are predetermined values.

Although in the above-described example, the processing in S1 to S6 is performed before the endoscope 2 is connected and an endoscopic image is displayed on the monitor 4, the processing in S1 to S6 may be performed at the time of generation of each frame image of an endoscopic image.

For example, it is possible that: the processing in S1 to S6 is performed each time a frame image is generated, and when first and second drive control signals for obtaining a next frame image are outputted, the drive control signals are corrected by correction amounts obtained by the above-described processing.

Or, the processing in S1 to S6 may be performed in response to an instruction from the surgeon.

For example, the processing in S1 to S6 may be performed upon the surgeon operating a predetermined switch during endoscopic observation.

Or, it is possible that: the temperatures are constantly detected by the processing in S2 and S3; and if there is a change that is equal to or exceeds a predetermined threshold value in the detected temperatures, the processing in S4 to S6 is performed.

Also, although in the above-described example, the drive signals for the actuator 15 are corrected using the correction coefficients, which are ratios relative to the reference displacement amounts, the drive signals for the actuator 15 may be corrected using correction amounts that are differences from the reference displacement amounts.

As described above, the above-described embodiment enables provision of a scanning endoscope apparatus that can suppress fluctuation of a two-dimensional scan pattern of illumination due to an individual difference of an actuator when the actuator is driven, without increase in outer diameter of an insertion portion.

As a result, a size of a display area of a subject displayed on the monitor 4 does not change, which prevents a surgeon from feeling odd.

The present invention is not limited to the above-described embodiment and various modifications, alterations and the like are possible without departing from the spirit of the present invention.

What is claimed is:

1. A scanning endoscope apparatus comprising:
   a light source configured to output illuminating light;
   an optical fiber inserted inside an insertion portion of an endoscope, the optical fiber being configured to guide the illuminating light from the light source disposed in a main body apparatus, from a proximal end to a distal end;
   a dielectric actuator disposed in the endoscope, the dielectric actuator being configured to drive the distal end of the optical fiber so that the illuminating light outputted from the optical fiber is scanned on a subject;
   a memory disposed in the endoscope, the memory being configured to store correlation information on a correlation relationship between a first parameter relating to a drive signal for driving the dielectric actuator and a second parameter unique to the dielectric actuator, the second parameter relating to a displacement amount of the dielectric actuator;
   a drive signal detection circuit disposed in the main body apparatus, the drive signal detection circuit being configured to detect the drive signal for driving the dielectric actuator; and
   a processor comprising hardware, the processor disposed in the main body apparatus, the processor being configured to correct the drive signal for driving the dielectric actuator, based on the correlation information and the drive signal detected by the drive signal detection circuit so that the displacement amount becomes a predetermined value irrespective of an individual difference of the dielectric actuator.

2. The scanning endoscope apparatus according to claim 1, wherein:
   the first parameter is the drive signal;
   the second parameter is the displacement amount; and
   the correlation information is a correlation coefficient between the drive signal and the displacement amount.

3. The scanning endoscope apparatus according to claim 2, wherein the correlation information includes a first correlation coefficient between the drive signal and a temperature, and a second correlation coefficient between the temperature and the displacement amount.

4. The scanning endoscope apparatus according to claim 3, wherein:
   the drive signal is a current signal; and
   the first correlation coefficient is a correlation coefficient between a value of the current signal and a value of the temperature.

5. The scanning endoscope apparatus according to claim 1, wherein the processor is further configured to correct a waveform of the drive signal.

6. The scanning endoscope apparatus according to claim 1, wherein the processor is further configured to correct the drive signal for driving the dielectric actuator, by correcting an output level of the drive signal based on a ratio of a displacement amount calculated, from the drive signal detected by the drive signal detection circuit, using the correlation information, relative to the predetermined value.

7. The scanning endoscope apparatus according to claim 1, wherein the dielectric actuator includes two actuators configured to move the distal end of the optical fiber in two directions perpendicular to each other.

8. The scanning endoscope apparatus according to claim 7, wherein the scan is scanning of the illuminating light in a spiral on the subject.

9. The scanning endoscope apparatus according to claim 7, wherein:
   the predetermined value includes two maximum displacement amounts at a time of maximum displacement in the two directions; and
   the processor is further configured to correct the drive signal for driving the dielectric actuator based on the correlation information and the drive signal detected by the drive signal detection circuit so that the respective displacement amounts of the two actuators at the time of maximum displacement become the maximum displacement amounts.

* * * * *